United States Patent [19]

Peyton et al.

[11] Patent Number: 4,509,081
[45] Date of Patent: Apr. 2, 1985

[54] OPTICAL SYSTEM FOR AUTOMATIC SORTING AND INSPECTION EQUIPMENT

[75] Inventors: John J. Peyton; Bryan K. Watt, both of Santa Barbara, Calif.

[73] Assignee: Industrial Automation Corp., Goleta, Calif.

[21] Appl. No.: 445,282

[22] Filed: Nov. 29, 1982

[51] Int. Cl.³ .................................................. H04N 7/18
[52] U.S. Cl. ............................ 358/225; 250/223 B; 358/106; 358/108
[58] Field of Search ............... 358/225, 106, 107, 108; 250/223 B

[56] References Cited

U.S. PATENT DOCUMENTS

| | | | | |
|---|---|---|---|---|
| 4,146,907 | 3/1979 | Jensen | ................................. | 358/225 |
| 4,167,756 | 9/1979 | Smith | ................................. | 358/225 |
| 4,280,624 | 7/1981 | Ford | ................................. | 358/106 |
| 4,414,566 | 11/1983 | Peyton | ................................. | 358/101 |

*Primary Examiner*—Howard W. Britton
*Attorney, Agent, or Firm*—Blakely, Sokoloff, Taylor & Zafman

[57] ABSTRACT

An optical system for automatic sorting and inspection machines for providing an improved two dimensional image of a three dimensional object to a camera or a camera-like device is disclosed. The optical system utilizes two spaced apart mirrors for receiving light primarily from different areas of the object to be viewed. Each mirror is positioned to reflect that light toward an optical axis. Positioned between the first and second mirrors are third and fourth mirrors positioned to reflect the light received thereby along the optical axis of the camera system. In this manner the image viewed by the camera will represent two separate views or image portions of the object being viewed, which image portions may or may not overlap as desired. By proper positioning of the mirrors, one can obtain an image of a three dimensional object which includes image portions of minimum distortion which effectively start to reach around the object and therefore not otherwise viewable from the camera position.

4 Claims, 5 Drawing Figures

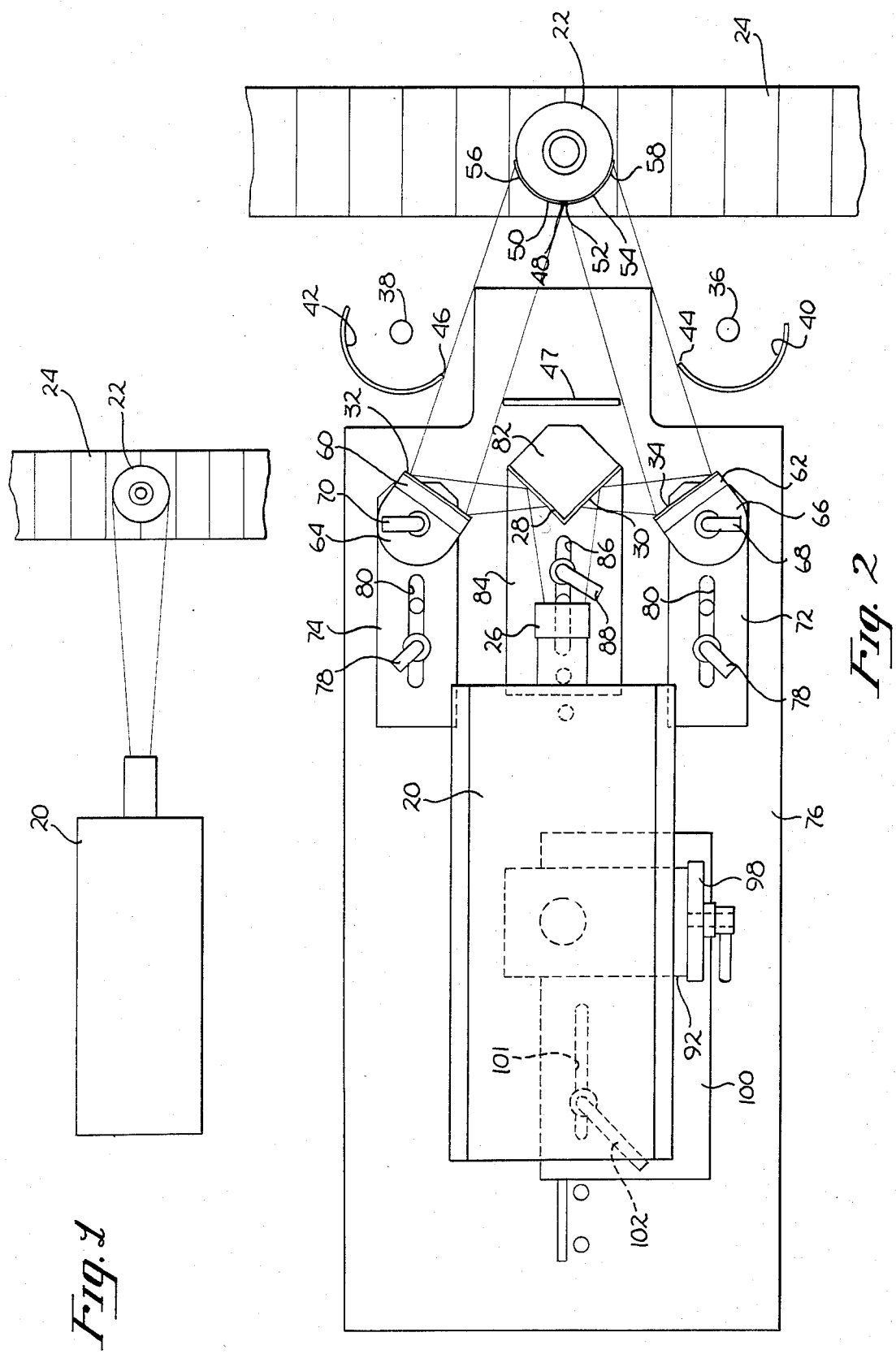

OPTICAL SYSTEM FOR AUTOMATIC SORTING AND INSPECTION EQUIPMENT

BACKGROUND OF THE INVENTION

1. Field of the Invention

The present invention relates to the field of automatic sorting and inspection systems, and more particularly to optical systems used in conjunction with automatic sorting and inspection systems.

2. Prior Art

The preferred embodiment of the present invention is intended for use in an automated bottle sorting system. Since that particular application is both illustrative of typical problems in the prior art and the solution provided by the present invention, the prior art directed to this particular application will be described.

Various types of bottle sorters are well known in the prior art, such machines being used, by way of example, for the sorting of returnable soft drink bottles. Obviously some bottles may be sorted based on bottle height and diameter and/or glass color, and accordingly, sorting machines based on various mechanical sensors and photodetectors are well known. Other machines having some form of linear array of sensors have been used to attempt to obtain more information regarding each bottle as each bottle passes the linear array. Another approach which may be expected to be used in future equipment, is to view each bottle with some form of camera system and then undertake some form of analysis of the image for identification purposes. Since the labels on soft drink bottles are almost always 180 degree labels, repeating on the other 180 degrees around the bottle, a bottle viewed from one side theoretically will present all information on the label regardless of the angular orientation of the bottle, the image portion going out of view at one side of the bottle as the bottle is rotated reappearing on the other side of the bottle. Obviously, the image will appear split, but at least the information in the image will theoretically be all there. However, in any practical system the camera must set relatively close to the bottle. Accordingly, the camera will view significantly less than 180 degrees of the bottle. Assuming that the bottles are not angularly aligned in general, not only will the image be a split image but the information in that image will now be somewhat sensitive to the bottle angular orientation, i.e., the nonviewable portion of the 180 degree image will be dependent upon the angular orientation of the bottle. The problem is aggravated somewhat by the fact that the label image is highly distorted near the edges thereof so that an additional part of the image is unsuitable for analysis and accordingly is effectively nonviewable also.

Because the useful image information presented to the camera system for any particular bottle type is somewhat bottle angular orientation dependent, a significant level of uncertainty in the bottle identification of any system will result, thereby making the sorting of bottles having similar (but not the same) labels difficult and/or subject to error. Accordingly, the preferred embodiment of the present invention is directed toward the minimization of errors from this source by providing a usable image approaching or even equal to a 180 degree wrap on the bottle being viewed.

BRIEF SUMMARY OF THE INVENTION

An optical system for automatic sorting and inspection machines for providing an improved two dimensional image of a three dimensional object to a camera or a camera-like device is disclosed. The optical system utilizes two spaced apart mirrors for receiving light primarily from different areas of the object to be viewed. Each mirror is positioned to reflect that light toward an optical axis. Positioned between the first and second mirrors are third and fourth mirrors positioned to reflect the light received thereby along the optical axis of the camera system. In this manner the image viewed by the camera will represent two separate views or image portions of the object being viewed, which image portions may or may not overlap as desired. By proper positioning of the mirrors, one can obtain an image of a three dimensional object which includes image portions effectively starting to reach around the object, and therefore not otherwise viewable from the camera position.

BRIEF DESCRIPTION OF THE DRAWINGS

FIG. 1 is a drawing illustrating the viewing of a circular object such as a bottle by a camera.

FIG. 2 is a top view of preferred embodiment of the present invention in the same application as illustrated with respect to FIG. 1.

DETAILED DESCRIPTION OF THE INVENTION

Figure 3:
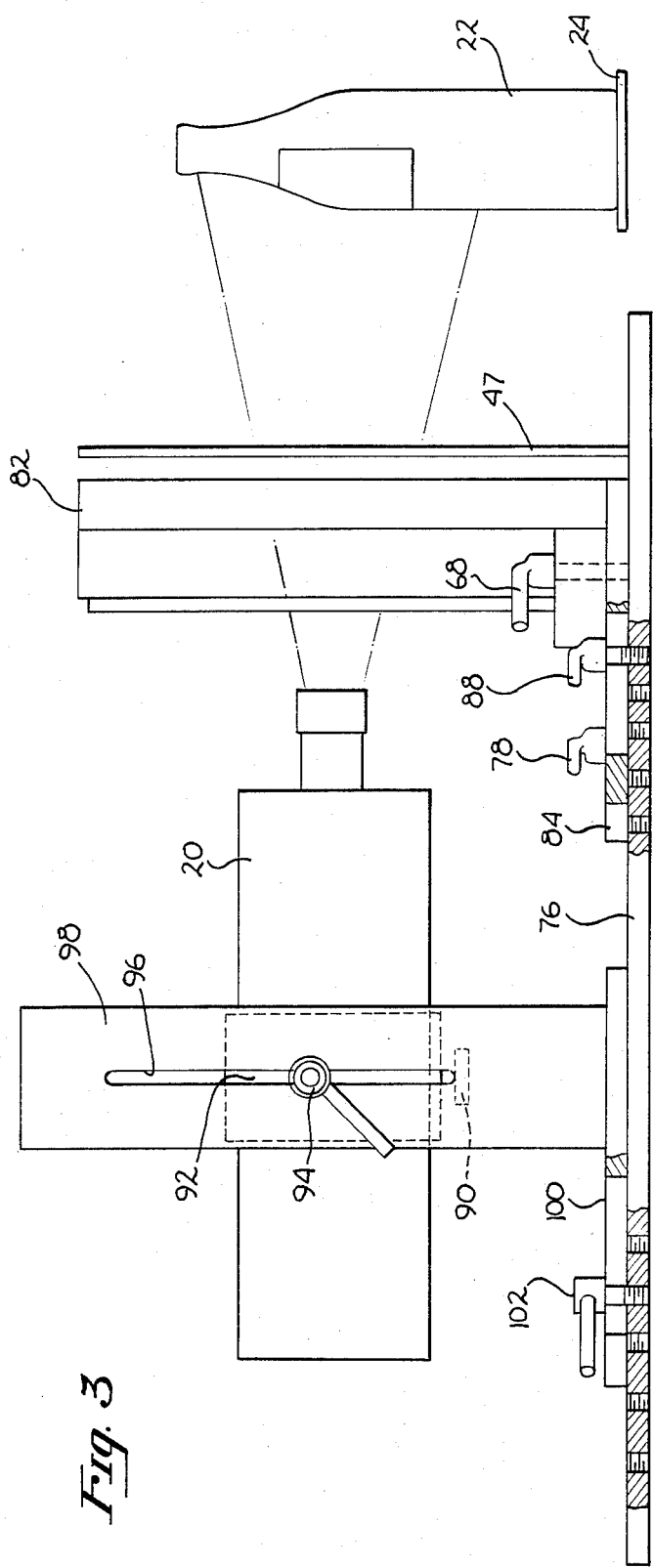
FIG. 3 is a side view in partial cross section of the invention of FIG. 2.

First referring to FIG. 1, an illustration of the use of an ordinary camera such as a video camera for viewing bottles on a conveyor may be seen. In the illustration the camera 20 is viewing a bottle 22 on a conveyor 24 to provide an image thereof having sufficient label information to allow analysis of the video signal for bottle identification purposes. It is apparent that the camera is viewing significantly less than a 180 degree image of the bottle. It is also apparent that the edges of the image perceived by the camera will be badly distorted so that some additional portion of the bottle image will not be usable for bottle identification purposes, and accordingly must be considered nonviewable from a system standpoint.

Now referring to FIG. 2, a view of the present invention in the same application as illustrated in FIG. 1 (but taken on a larger scale) may be seen. As before, bottle 22 is presented to camera 20 on conveyor 24. The camera lens 26 however, is not directly viewing the bottle 22, but instead is looking into mirrors 28 and 30 disposed approximately 45 degrees with respect to the optical axis of the lens system of the camera. A second pair of mirrors 32 and 34 are disposed outward from mirrors 28 and 30 respectively to reflect light received from bottle 22 to the mirrors 28 and 30. In the preferred embodiment, strobe lights 36 and 38, together with their reflectors 40 and 42, are triggered as each bottle reaches the position shown to provide a strobed still image of the moving bottle. In the preferred embodiment, mirrors 40 and 42 for the strobes 36 and 38 are adjustable in position so that the edges 44 and 46 thereof serve the limit the field of view of the bottle. Also an adjustable plate such as plate 48 may be used to similarly limit the extent of each image portion.

Figure 5:
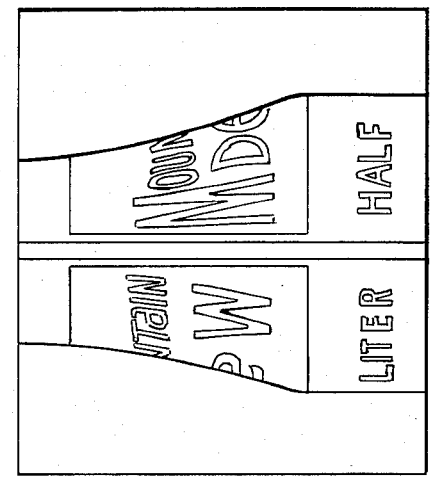
FIGS. 4 and 5 illustrate the image viewed by the camera in the present invention when viewing a bottle at two different angular orientations.
Figure 4:
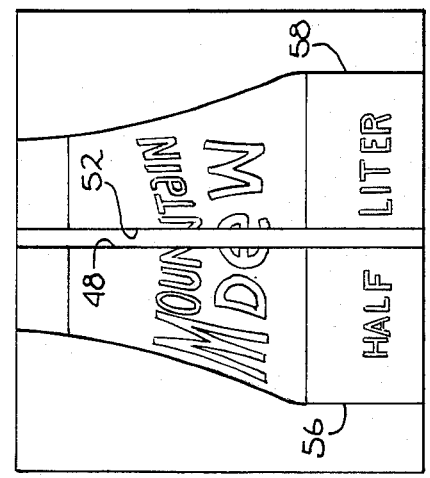

In the system with which the preferred embodiment of the present invention is used, the bottles are presented on the conveyor 24 in a steady stream in contact with one another, rather than being separated as suggested by FIG. 1. Accordingly, adjacent bottles are contacting the bottle being viewed at two points 180 degrees apart, so that still a full 180 degree image cannot be obtained in such a system. It may be seen from FIG. 2 however, that by proper limiting of the image portions being viewed, the right edge 48 of the image of the left side 50 of the bottle can be made substantially coterminous with the left edge 52 of the image of the right side 54 of the bottle. This is illustrated in FIGS. 4 and 5, representing the image which would be seen on a video monitor when using a video camera for camera 20. One could bring the two half images together if desired, though their separation is of no consequence in the preferred embodiment of the invention, as the image analysis technique used is insensitive to the separation.

Referring again to FIG. 2, it will be seen that the left edge 56 of the image of the left side 50 of the bottle is slightly truncated by the edge 46 of reflector 42, and that the right edge 58 of the image of the right side of the bottle 54 is similarly truncated by the edge 44 of strobe reflector 40. This, of course, is done in the preferred embodiment to prevent picking up any part of the image of adjacent bottles, and has the net effect of still limiting the viewable image to somewhat less than a 180 degree wrap on the bottle. However, even with this slight loss, the images of the bottle obtained with the present invention are far superior to that obtained without the use of the invention, as the wrap of the image obtained is substantially closer to 180 degrees than without the present invention. Further, as may be seen in both FIG. 2 and FIGS. 4 and 5, the outer edges of the image portions are not defined by a tangential view of the bottle edge, but are defined by a form of aperture means so that the image distortion adjacent the outer edges of the image portions is substantially less than is obtained without the present invention, thereby making substantially all of the viewable image usable for image analysis purposes. Further, the apparent image wrap of the image portions of any part of a label on the neck of the bottle may be as large as, or even slightly larger than, 180 degrees because of the absence of truncation in the neck region. Consequently, while the outer edges of the neck region image portions may taper off to excessive distortion, the useful wrap obtained in the present invention for the neck region may still be substantially equal to 180 degrees.

FIGS. 4 and 5 illustrate the two image portions of a bottle as viewed by the camera, FIG. 4 representing one angular position of the bottle and FIG. 5 representing another. It may be seen that the net effect is that the two image portions taken together effectively represent substantially all of the information on a 180 degree label wrap on the bottle, with the information disappearing from one image portion as the bottle is rotated reappearing as part of the other image portion.

Now referring to FIGS. 2 and 3, details of the structure of the preferred embodiment may be seen. Since the preferred embodiment of the present invention is intended to be used with a bottle sorter which may be set up to sort bottles of various sizes (the bottles being sorted generally already having been roughly sorted as to size) it is important that the optical system be readily adjustable as required. Mirrors 32 and 34 are mounted on vertically standing rectangular plates 60 and 62 which in turn are welded to footlike members 64 and 66 respectively. Manually operable thumb screw members 68 and 70 threadedly engage slide plates 72 and 74 respectively, to lock the mirrors with respect thereto at the desired angular orientation. The slide plates 72 and 74 in turn may be locked to base plate 76 by thumb screws 78. A plurality of threaded holes in the base plate 76 is provided for this purpose, with the thumb screws providing the only reference to the base plate. This, in combination with the cooperative slots 80 in plates 72 and 74 allows for a wide adjustment in the lateral position of the mirrors, sliding in the slots and/or movement of the respective thumb screws to another position, and further allows an adjustment in the separation of mirrors 32 and 34 by the rotation of plates 72 and 74 around their thumb screw mounts.

Mirrors 28 and 30 are also vertically oriented rectangular mirrors like mirrors 32 and 34, and are mounted on block 82 fastened to slide plate 84. This plate, like the others, is provided with a slot 86 and is lockable with respect to the base plate 76 by thumbscrew 88. Finally, camera 20 is mounted to an L-shaped support by screw 90, the vertical portion 92 of the L-shape support being threaded to receive lock screw 94 adjustable in vertical position as a result of slot 96 in vertical plate 98. Plate 98, on the other hand, is welded to a still further slide plate 100, also having an adjustment slot 101 and lockable with respect to base plate 76 by lock screw 102. Accordingly, the camera is adjustable both in a vertical direction and laterally with respect to the bottles being viewed. If desired, a slide may be provided between mounting plate 100 and base plate 76 so that the camera cannot rotate about a vertical axis during adjustment.

The system of the present invention, of course, can be initially adjusted by placing a bottle at the target position and with adequate illumination thereof, viewing the image portions of the target bottle on a video monitor as the mirror and other adjustments are made. The adjustments can then be double checked by operating the system in the intended manner and again viewing the image portions on a monitor to be sure that strobe firing is occurring at the proper bottle position and that the image portions are as desired. The net result, as stated before, is that the total image received by the camera can be made to represent much closer to a 180 degree wrap of the label region of a bottle than could be achieved without the present invention, even when bottles are back to back on a conveyor system.

Obviously the present invention is not limited to bottle sorting applications, but could also be used for label inspection purposes on paper label containers, by way of example, whether on beverage containers or other containers. By way of specific example, some medication containers having a paper label applied to a substantially square cross section glass or plastic container, with the label in some cases wrapping around two or more sides of the container. Labels on such containers presented individually on a conveyor could readily be inspected by the present invention using a single camera, as the present invention would allow the unwrapping of the label image from a full three sides of the container. Thus, while the preferred embodiment of the present invention has been disclosed and described with respect to a preferred embodiment and the preferred usage thereof, it will be obvious to those skilled in the art that various changes in form and detail may be made therein as desired for other applications to provide improved two dimensional images of three dimensional objects.

We claim:

1. A system for providing a video signal containing image portions of a container label representing an approximately 180 degree wrap of the label region thereof comprising a conveyor means for providing a steady stream of containers substantially contacting each other along a conveyor path;

a video camera for receiving an image along the optical axis thereof approximately perpendicular to said conveyor path and providing a video signal in response thereto;

a first mirror for receiving light from a first area of a target container located substantially on the said optical axis of said video camera;

a second mirror for receiving light from a second area of the target container; and third and fourth mirrors adjacent said optical axis and positioned to reflect light from said target container and reflected by said first and second mirrors, respectively, along said optical axis, whereby said video camera may receive an image comprised of a first image portion of the first area of the target container and a second image portion of the second area of the target container, said first and second areas of the target container being substantially contiguous along one edge thereof and collectively representing an approximately 180 degree wrap of the container extending from adjacent the area of contact of the container into the next preceeding container on said conveyor means to adjacent the area of contact of the container with the next succeeding container on said conveyor means, said first and second image portions having sufficiently low image portions having sufficiently low image distortion over said first and second areas that said video camera will provide a video signal containing substantially all the detail of said first and second areas.

2. The system of claim 1 wherein said optical system further includes aperture means for adjusting the edges of said first and second image portions to eliminate any image portion of an area of the next preceeding and succeeding containers.

3. A method of providing a video signal containing image portions of a container label which collectively represent an approximately 180 degree wrap comprising the steps of (a) conveying a stream of containers along a conveyor path and past a target position thereon, each container substantially contacting the adjacent containers, the containers having labels thereon repeating over each 180 degree segment thereof (b) providing a video camera for receiving an image along the optical axis thereof, which optical axis is substantially perpendicular to the conveyor path and directed through the center line of a container moving the target position (c) providing a first mirror for receiving light from a first area of the label of a target container at the target position, the first area comprising the area of the label extending approximately 90 degrees from adjacent the region of contact into the next succeeding container to the optical axis of the video camera (d) providing a second mirror for receiving light from a second area of the label of a target container at the target extending approximately 90 degrees from adjacent the region of contact with the next preceeding container to the optical axis of the video camera (e) providing third and fourth mirrors adjacent said optical axis and positioned to reflect light from said target container and reflected by the first and second mirrors, respectively, along the optical axis, whereby the video camera may receive an image comprised of a first image portion of the first area of the target container and a second image portion of the second area of the target container, the first and second areas of the target container being substantially contiguous along one edge thereof and collectively representing almost a 180 degree wrap of the container label, the first and second image portions having sufficiently low image distortion over the first and second areas that the video camera will provide a video signal containing substantially all the detail of the first and second areas and to the exclusion of any part of the label of the two adjacent containers.

4. The method of claim 3 wherein the first and second mirrors are spaced apart at each side of the optical axis of the video camera so that the included angle between the two lines joining the center of each mirror and the center of the target container is substantially less than 90 degrees.

* * * * *